United States Patent [19]

Bakonyi et al.

[11] Patent Number: 4,675,413

[45] Date of Patent: Jun. 23, 1987

[54] PROCESS FOR THE PREPARATION OF BENZIMIDAZOLE-THIOL

[75] Inventors: Mária Bakonyi, Budapest; György Lugosi, Göd-felso; Tamás Kállai, Budapest; Maria Hima née Tóth, Budapest; Tibor Montai, Budapest; Mária Sziládi, Budapest, all of Hungary

[73] Assignee: Chinoin Gyogyszer es Vegyeszeti Termekek Gyara rt, Budapest, Hungary

[21] Appl. No.: 811,246

[22] Filed: Dec. 19, 1985

[30] Foreign Application Priority Data

Dec. 19, 1984 [HU] Hungary ............................. 4725/84

[51] Int. Cl.⁴ ........................................... C07D 235/04
[52] U.S. Cl. .................................... 548/329; 548/306
[58] Field of Search ................................. 548/306, 329

[56] References Cited

U.S. PATENT DOCUMENTS 2,666,764   1/1954   Lanzilotti et al. ................. 548/329

*Primary Examiner*—John M. Ford
*Assistant Examiner*—Robert C. Whittenbaugh
*Attorney, Agent, or Firm*—Karl F. Ross; Herbert Dubno; Jonathan Myers

[57] ABSTRACT

A new process is disclosed for preparing a compound of the formula (I)

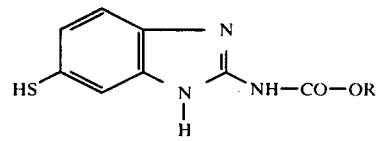

wherein R is $C_1$ to $C_5$ alkyl; which comprises reducing a compound of the formula (II)

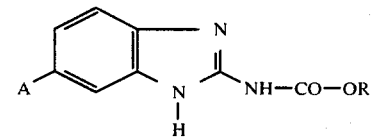

or salt thereof wherein
A is $-SO_2X$, $-SOH$, $-SOA^1$, or $-SA^1$ group,
X is chlorine or hydrogen; and
$A^1$ is a group of the Formula

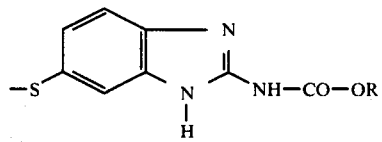

with the aid of aluminum activated with a catalytic amount of a metal and/or metal salt in a mixture of water, a mineral acid, and an aliphatic carboxylic acid having 1 to 3 carbon atoms at a temperature of 0° to 100° C., thereafter, optionally, the product is recovered from an acid medium at a pH range of 2 to 3 in crystalline form.

5 Claims, No Drawings

PROCESS FOR THE PREPARATION OF BENZIMIDAZOLE-THIOL

TECHNICAL FIELD

The present invention relates to a novel process for the preparation of the benzimidazole-thiol derivatives of the formula (I)

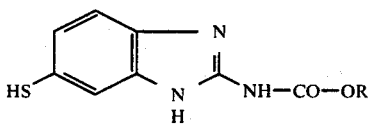
(I)

wherein
R is alkyl having 1 to 5 carbon atoms,
by reducing the compounds of the formula (II)

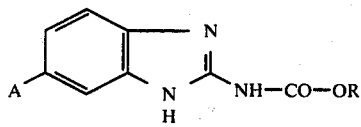
(II)

wherein
A is $-SO_2X$, $-SOH$, $-SOA^1$ or $-SA^1$,
X is hydrogen or chlorine,
$A^1$ is a group of the formula

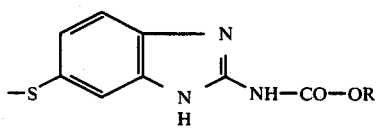
$(A^1)$

R is the same as defined hereinabove
and/or the salts thereof by the aid of a metal in the presence of water and a mineral acid. According to the process the reduction is carried out in a mixture of water, mineral acid and aliphatic carboxylic acid having 1 to 3 carbon atoms by the aid of aluminum or aluminum activated with a catalytic amount of a metal and/or metal salt at a temperature of 0° to 100° C., thereafter, if desired, the product is recovered from an acidic medium preferably at a pH of 2 to 3 in a crystalline form.

The definition of substituents R, A, X and $A^1$ is always the same in the whole description.

BACKGROUND ART

The compounds of the formula I are known. They are intermediates in the process for the preparation of the biologically active 2-alkoxy-carbonylamino-benzimidazole derivatives. There has been known only two processes for the preparation of the isolated product so far.

According to the working example of Hungarian Patent Specification No. 177,418 bis[(2-methoxycarbonyl)-amino-benzimidazole-5(6)-yl]-disulphide is reduced with sodium metal in liquid ammonia, then the thiol is liberated from the sodium salt thiol-compound remaining after the evaporation of the ammonia. The disadvantage of the above process is that it is quite difficult to carry out from an industrial point of view, expensive equipment should be employed and as both sodium metal and liquid ammonia are dangerous to handle, special security measures have to be followed to. The melting point of the product prepared according to the example is 260° to 262° C.

According to Hungarian Patent Specification No. 182,782 the product is prepared from the hydrochloric salt of a sulphonic chloride falling under the scope of the formula II with metals in the presence of water and mineral acid. Tin, zinc and iron were exemplified as reducing agents. In all cases the reduction resulted in the corresponding metal salt of the thiol of the formula I, which precipitated from the given reaction mixture and thus it could be isolated. According to the only example relating to the preparation of the isolated thiol, the tin salt of the thiol obtained as a product of the reduction was decomposed by hot sodium carbonate solution, the insoluble tin hydroxide was removed by filtration and the thiol was recovered from the filtrate. This method is lengthly and quite great losses occur as the thiol oxidizes to the corresponding disulphide in a quite short period. A further problem is that it is very difficult to purify the product from the tin contamination, it can only be obtained in several stages and leads to losses. Therefore according to the above specification in order to avoid the difficulties accompanying the separation of the thiol, the metal salts were further reacted. Thus the metal contaminations could be eliminated in a further stage of the reaction.

As to the metals used in the above specification we have to note that the highest yield could have been achieved when tim was used. However, the price of tin is high, therefore this process is uneconomic. Zinc has a high ability to form complexes and this results in different problems, while the yield is not satisfactory when iron is employed.

Considering these difficulties it is strange that the above specification does not mention that aluminum could be used.

By improving the known methods a simple, economic process was seeked for the preparation of the thiole of the formula I, which enables the industrial scale production of the said thiol in an easy manner and results in a pure product.

DETAILED DESCRIPTION OF THE INVENTION

Surprisingly we found that aluminum is very useful in the reduction and by using aluminum pure product can be achieved even on an industrial scale. In order to improve the yields the use of a suitably active aluminum is required, e.g. the use of aluminum foil with high surface. The cruder, commercial sorts of aluminum, e.g. aluminum grist, chip, or any kind of flitter may also be used, but the yield will only be satisfactory if they are activated in a suitable manner.

According to our invention the metals belonging to the group of IV, II and/or VIII/a of the periodical system, preferably tin, lead, magnesium, zinc, mercury or iron optionally in the form of salts were found to be suitable for the activation. The other metals are not appropriate for this purpose according to our examinations.

The above-mentioned metals or metal mixtures can also be used in the form of salts as they are transformed into metals in the given reductive medium. The amount of the activating metal is practically 0 to 5% by weight calculated for aluminum.

If tin is used as activator in the process, it is very useful that the unused aluminum and tin can be filtered out and recycled to the process after the supplementing consumed aluminum. Thus in the case of continuous operation tin introduced into the process can be used theoretically without losses, practically with some recyclization loss.

The present invention is further based on the recognition that the reaction medium also has a significant influence on the increase of the yields. It was found that it is not sufficient to assure an acidic medium only, but it is preferable to employ a mixture of an aqueous mineral acid, preferably hydrogen bromide and an organic acid having 1 to 3 carbon atoms, preferably formic acid. If sulphochlorides are used as starting materials, the organic acid inhibits the precipitation of disulphide formed as an intermediate being badly soluble in the said medium.

According to our invention the well-isolatable endproduct of the process is the pure thiol in contradiction with the process according to Hungarian Patent Specification No. 182,782 wherein tin or zinc was used and the metal salt of the thiol was obtained, purification of which is difficult.

As the melting point of the product of the formula I wherein R=methyl prepared according to our process is 435° C. which is much higher than that of the product obtained in the Hungarian Patent Specification No. 177,418 and as the Hungarian Patent Specification No. 182,782 does not present any melting point data the endproducts are characterized by elemental analysis data (which does not indicate the presence of the disulphide derivative falling under the scope of the formula II as a result of the similarity of their elemental composition), it was considered to be necessary to analyse thoroughly our product.

Besides the determination of the elemental composition, the molecular weight was also measured by mass spectroscopic method and a method was also worked out for controlling the purity of the product by thin-layer chromatography taking into special consideration that the disulphide of the formula III may be a possible contamination. It was found that the molecular weight of our said product is 223, which value corresponds to the compound of formula I, wherein R=methyl. According to the thin-layer chromatographic examination this product comprises a contaminating substance which is proved to be 1 to 2% by weight of disulphide of formula II according to its $R_f$ value.

From the said product (after isolation or without isolation) [5-(propylthio)-1H-benzimidazole-2-yl]-carbamic acid methyl ester of high purity was prepared in a yield of 90% by propylation.

The invention is illustrated by the following, non-limiting examples.

EXAMPLE 1

32.62 g of 2-[(methoxycarbonyl)-amino]-1H-benzimidazole-5-sulphonylchloride hydrochloride salt are added to a mixture of 80 ml of formic acid, 120 ml of water and 40 ml of 50% hydrogen bromide under stirring, thereafter 10 g of aluminum foil torn to pieces are added to the reaction mixture. The addition of aluminum is accompanied by the slight evolution of hydrogen.

The reaction mixture is stirred at a temperature of 35° to 40° C. for 1.5 hours, then at a temperature of 60° to 65° C. for 30 minutes, thereafter it is cooled to a temperature of +5° C. The aluminum which did not dissolve is filtered out; its weight is 3 g. The pH of the filtrate is adjusted to 2–3 by adding 80 ml of 40% sodium hydroxide solution. The precipitated white crystals are filtered off washed with water, covered by methanol and dried.

19.6 g of 2-[(methoxycarbonyl)amino]-1H-benzimidazole-5(6)-thiol are obtained. Yield: 87%. Melting point: 435° C. Ash content: 0.2 to 0.5%. According to the thin-layer chromatographic examination it comprises only one contaminating substance, which is proved to be 1 to 2% of bis[(2-(methoxycarbonyl)-amino)-benzimidazole-5(6)-yl]-disulfide according to its $R_f$ value.

Elemental analysis of the product: Calculated: C% 48.20 H% 3.90 N% 18.6 S% 14.30. Found: C% 48.42 H% 4.06 N% 18.82 S% 14.36.

EXAMPLE 2

32.62 g of 2-[(methoxycarbonyl)-amino]-1H-benzimidazole-5-sulphonylchloride hydrochloride salt are suspended in 120 ml of water, then 15 g of aluminum chips of 2 to 3 cm (commercially avaialble waste), 0.5 g of tin powder are added and the mixture is stirred at a temperature of 10° to 15° C. for 20 minutes.

In a separate vessel 80 ml of 99% formic acid and 40 ml of 50% aqueous hydrogen bromide are mixed and this solution is added dropwise to the reaction mixture within 0.5 hours at a temperature of 10° to 15° C. under cooling with saline. Then the reaction mixture is stirred at a temperature of 35° to 40° C. for 1.5 hours and at a temperature of 60° to 65° C. for 0.5 hours. The undissolved metals are filtered off from the cold solution (their weight is 8 g).

The pH of the filtrate is adjusted to 2 to 3 by addition of 80 ml of 40% aqueous sodium hydroxide solution under cooling. The precipitated white solid is filtered off, washed with water and methanol and dried. Thus 20 g of 2-[(methoxycarbonyl)-amino]-1H-benzimidazole-5(6)-thiol are obtained as a product. (Yield: 90%)

The quality of the product is the same as that of the product prepared according to Example 1.

EXAMPLE 3

32.62 g of the hydrochloride salt of 2-[(methoxycarbonyl)-amino]-1H-benzimidazole-5-sulphonyl chloride are suspended in 120 ml of water, the undissolved metal residue having a weight of 8 g filtered off after the reaction according to Example 2, comprising tin and aluminum, is added, then 7 g of commercial aluminum flitter are added and the mixture is stirred at a temperature of 10° to 15° C. for 20 minutes.

Further the process of Example 2 is followed.

The product is 20.14 g of 2-[(methoxycarbonyl)-amino]-1H-benzimidazole-5(6)-thiol.

The quality of the product is the same as that of the product prepared according to Example 1.

EXAMPLE 4

The process according to Example 2 is followed except that acetic acid of the same amount is used instead of formic acid in the reaction. The product can be recovered e.g. as follows:

(a) The undissolved metals are filtered off from the reaction mixture after the reduction the filtrate is diluted with 1500 ml of water, the precipitated white crystals are filtered off, washed with water and methanol and dried. The product is 16.7 g of 2-[(methoxycarbonyl)-amino]-1H-benzimidazole-5 6-thiol.

(b) After finishing the reduction the undissolved metals are filtered off, thereafter the pH of the reaction mixture is adjusted to 5 under cooling by adding about 70 ml of 40% aqueous sodium hydroxide solution dropwise at room temperature. The precipitated crystals are isolated. The product is 19 g of 2-[(methoxycarbonyl)-amino]-1H-benzimidazole-5(6)-thiol.

The quality of the product thus obtained is the same as that of the product prepared according to Example 2.

EXAMPLE 5

To the solution of 80 ml of 99% formic acid, 120 ml of water and 40 ml of 50% aqueous hydrogen bromide 6 g of aluminum flitter are added and the reaction mixture is stirred for 15 minutes at a temperature of 10° to 15° C. Then 0.3 g of tin powder and 22.2 g of bis[(2-(methoxycarbonyl)-amino)-benzimidazole-5(6)-yl]-disulphide are added and the solution is stirred for 1.5 hours at a temperature of 30° to 40° C.

(At the beginning of the reaction slight gas- and heat evolution can be observed which ceases later and gentle heating is needed to maintain the suitable temperature.) Then the reaction mixture is cooled to a temperature of 5° C., the undissolved metals are filtered off, the pH of the filtrate is adjusted to 2 to 3 by the addition of 80 ml of 40% aqueous sodium hydroxide solution. The precipitated white crystals for filtered off, washed with water and methanol and dried. The product is 20.05 g of 2-[(methoxycarbonyl)-amino]-1H-benzimidazole-5(6)-thiol.

The quality of the product is the same as that of the product prepared according to Example 1.

EXAMPLES 6 TO 12

The process of Example 2 is followed except that the mineral acid, activating additive and the temperature of the reduction is changed as listed in the following table.

| No. of the Example | Mineral acid | Reaction temperature °C. | Activating additive | Yield g |
|---|---|---|---|---|
| 6 | 40 ml of 50% aqueous HBr | 35–65 | 1 g SnCl$_2$.2H$_2$O | 19.8 |
| 7 | 60 ml of 50% aqueous HBr | 35–40 | 0.5 g Sn-powder | 19.9 |
| 8 | 33 ml cc. HCl | 35–65 | 0.5 g Sn-powder | 16.7 |
| 9 | 40 ml of 50% aqueous HBr | 35–65 | 1.2 g Pb/CH$_3$COO/$_2$ | 19.0 |
| 10 | 40 ml of 50% aqueous HBr | 20–60 | 4 g HgCl$_2$ | 12.3 |
| 11 | 40 ml of 50% aqueous HBr | 55–70 | 2 g Fe powder | 13.0 |
| 12 | 40 ml of 50% aqueous HBr | 55–70 | 3 g FeSO$_4$.5H$_2$O | 13.5 |

Comment:
When copper and nickel salts were used as additives, the result was not satisfactory.

EXAMPLE 13

Transformation of the Product 22.3 g of 2-[(methoxycarbonyl)-amino]-1H-benzimidazole-5(6)-thiol are suspended in 200 ml of water and the suspension is cooled to 10° C. Then 80 ml of 40% aqueous sodium hydroxide solution are added under cooling which results in the dissolution of the thiol of the formula I. The reaction mixture is clarified with 1 g of activated carbon at a temperature of 10° to 15° C. and filtered. 100 ml of methanol and 14 ml of n-propylbromide are added to the filtrate and it is heated to 40°–45° C. and stirred for 1 hour. After some minutes the precipitation of the [5-(propylthio)-1H-benzimidazole-2-yl]-carbamic acid methyl ester starts. After the reaction is finished, the white crystalline substance is filtered off, washed with 300 ml of water, slurried with 100 ml of 5% aqueous formic acid, filtered, washed to neutral with water, covered with methanol, filtered and dried at a temperature of 50° C. Its weight is 23.8 g, which is the 90% of the calculated yield.

The quality of the product meets the requirements of the international standards set against the medicinal basic materials.

COMPARATIVE EXAMPLES

Example 14

The procedure of Example 2 is followed except that formic acid is not used in the reaction and the amount of the 50% aqueous hydrogen bromide is increased to 80 ml from 40 ml.

Thus the insoluble HBr salt of the disulphide of the compound of the formula III precipitates in the course of the reaction which is filtered off at the end of the reaction together with the undissolved metals. The product is isolated from the filtrate according to Example 2. Th weight of the product is 6.7 g which corresponds to the 30% of the calculated yield.

Example 15

The procedure of Example 2 is followed except that tin is not employed in the reduction.

20 g of product are obtained which is the mixture of the thiol of the formula I and the disulphide falling under the score of the formula II.

This product is added to 200 ml of 10% aqueous sodium hydroxide solution under stirring when the thiol of the formula I dissolves, while the disulphide of the formula II remains undissolved, thus the two substances can be separated by filtration. By adjusting the pH of the solution the thiol of the formula I can be precipitated. The yield is 40 to 70 % depending on the activity of the aluminum employed.

We claim:

1. Process for the preparation of a compound of the formula I

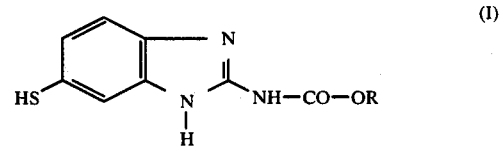
(I)

wherein R is alkyl having 1 to 5 carbon atoms by reducing a compound of the formula II or the salts thereof

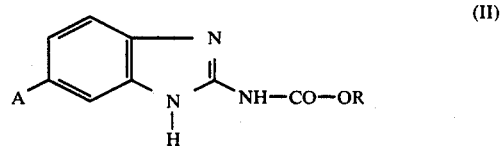
(II)

wherein
A stands for SO$_2$X, —SOH, —SOA$^1$ or —SA$^1$ group,
X is chlorine or hydrogen, $A^1$ represents a group of the formula

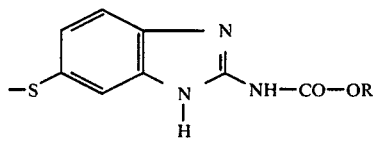
(A¹)

R is the same as defined hereinabove;
by the aid of a metal in the presence of water and a mineral acid, which comprises reducing a compound of the formula II, by the aid of aluminum or aluminum activated with a catalytic amount of a metal and/or metal salt additive wherein the metal is tin, lead, magnesium, zinc or iron in a mixture of water, mineral acid and an organic aliphatic carboxylic acid having 1 to 3 carbon atoms at a temperature of 0° to 100° C., thereafter, optionally recovering the product from an acidic medium in crystalline form.

2. The process as claimed in claim 1, which comprises using haloid acids, as mineral acid and using formic acid as aliphatic carboxylic acid.

3. The process as claimed in claim 1, which comprises using tin or lead optionally in the form of a salt for the activation of aluminum.

4. The process as claimed in claim 1, which comprises recovering the activating metal additive and using it repeatedly.

5. 2-[(methoxycarbonyl)-amino]-1H-benzimidazole-5(6)-thiol having a melting point of approximately 435° C. and the salts thereof.

* * * * *